United States Patent
Lo Gerfo

(12) 
(10) Patent No.: US 6,410,242 B1
(45) Date of Patent: Jun. 25, 2002

(54) METHOD FOR PRESERVING THE UNIQUENESS AND IDENTITY OF AN INDIVIDUAL

(76) Inventor: Paul F. Lo Gerfo, 979 Rte. 9W, Grandview, NY (US) 10960-4907

( * ) Notice: Subject to any disclaimer, the term of this patent is extended or adjusted under 35 U.S.C. 154(b) by 0 days.

(21) Appl. No.: 09/608,519

(22) Filed: Jun. 30, 2000

(51) Int. Cl.⁷ .................................................. C12Q 1/68
(52) U.S. Cl. ........................ 435/6; 435/320.1; 434/297; 536/23.5; 536/24.5
(58) Field of Search ............................... 536/23.5, 24.5; 435/320.1, 6; 434/297

(56) References Cited

U.S. PATENT DOCUMENTS 5,032,501 A * 7/1991 Milner .......................... 435/6
5,593,832 A * 1/1997 Glassberg ..................... 435/6
5,811,262 A * 9/1998 Yang .......................... 435/69.1
5,917,124 A * 6/1999 Gordon et al. ................. 800/18

OTHER PUBLICATIONS

Frederick M. Ausubel et al, Current Protocols In Molecular Biology, vol. 1, Feb. 1997.*

* cited by examiner

*Primary Examiner*—James Ketter
(74) *Attorney, Agent, or Firm*—Kirkpatrick & Lockhart LLP

(57) ABSTRACT

Apparatus and methods for preserving the uniqueness and identity of an individual as well as a method for isolating and preserving DNA for visual display are disclosed. Fluid or tissue samples taken from an individual are processed to separate the DNA from the other cell components. The DNA is placed in an alcohol and water based solution that causes the precipitation and suspension of the DNA so that it becomes visible to the naked eye. The DNA bearing solution is placed in a transparent capsule that can be further mounted in a desirable display structure.

29 Claims, 12 Drawing Sheets

METHOD FOR PRESERVING THE UNIQUENESS AND IDENTITY OF AN INDIVIDUAL

FIELD OF INVENTION

This invention relates generally to methods and apparatus for isolating genetic material from an organism to preserve its uniqueness and identity. More particularly, the invention relates to the preservation and visual display of DNA extracted from an organism.

BACKGROUND OF THE INVENTION

From the development of the chromosomal theory of inheritance by Austrian monk, Gregor Mendel, in the late nineteenth century to the description of the double helix by James D. Watson and Francis H. Crick in the 1950's, scientists and laypersons alike have been fascinated by the knowledge of chromosomes that are comprised of DNA (deoxyribonucleic acid). As is well known in the art, DNA chains compose the basic units of heredity, commonly referred to as genes. Genes formed from DNA acts as the blueprint from which an individual is created. Even more so than a fingerprint, an individual's full compliment of DNA distinguishes that individual from all others.

For decades, DNA has been studied for purely scientific, biological and medical purposes, e.g., to understand how it controls the development and combination of a myriad of organic and inorganic components into a life form such as Homo sapiens. Little attention has been paid to the aesthetic beauty of the structure or its value as a means of preserving the identity and memory of an individual.

DNA inherently has spiritual, commemorative and artistic value that has been overshadowed by the scientific implications of the biological material. Because of the uniqueness of each individual organism's DNA composition, DNA provides a means for memorializing and celebrating the organisms, whatever its form. DNA provides the perfect vehicle to enable an individual to preserve, exchange and display a declaration, memorial or commemorative of the life of one living being for the benefit of others. DNA can further be used to symbolize relationships among living individuals as well as act as living memorials to celebrate one's life events such as births, engagements and holidays rather than death. The small size of a full compliment of DNA material from an individual lends itself to being compartmentalized in keepsake items such as jewelry.

A sea change in the attitudes of individuals, particularly baby-boomers, about traditional funeral services and death has lead to a substantial increase in cremations and has revealed a void in how an individual is eulogized and remembered. There is a need for a way to remember an individual that will preserve the uniqueness of that individual for time immemorial.

Accordingly, it is an object of the invention to preserve DNA for, among other reasons, to preserve the memory of an individual. Another object is to suspend DNA in a capsule or container through which DNA can be displayed. These and other objects will become apparent from a reading of the following summary and detailed description of the invention.

SUMMARY OF THE INVENTION

The invention provides a means and apparatus to preserve the uniqueness and identity of a living being. DNA, extracted from the living being, is placed in a solution that causes it to precipitate and become visible to the naked eye. The DNA containing solution is placed in an aesthetically pleasing container fashioned to hold the DNA solution. The container becomes a permanent memorial that can be kept and displayed by interested parties such as relatives.

Specifically, the invention involves obtaining tissue or fluid samples from a living or dead organism (human being, animal, plant, bacterium or virus) and separating out selected cells for processing. The selected cells, for example, white blood cells in human blood, are processed to separate and isolate the cells' DNA component. The DNA component is exposed to a series of solutions to cause the DNA to precipitate out into a visible mass of string like formations. Due to the solubility properties of the solutions used, the DNA coalesces into a rough spherical shape that remains suspended in solution. The suspended DNA is then placed in a suitable storage vial or capsule for display.

The DNA laden vial or capsule can be mounted in a wide variety of stands or containers for display. These and other advantages of the invention will become apparent from a review of the drawings and a reading of the following detailed description.

DETAILED DESCRIPTION OF THE INVENTION

Figure 3:
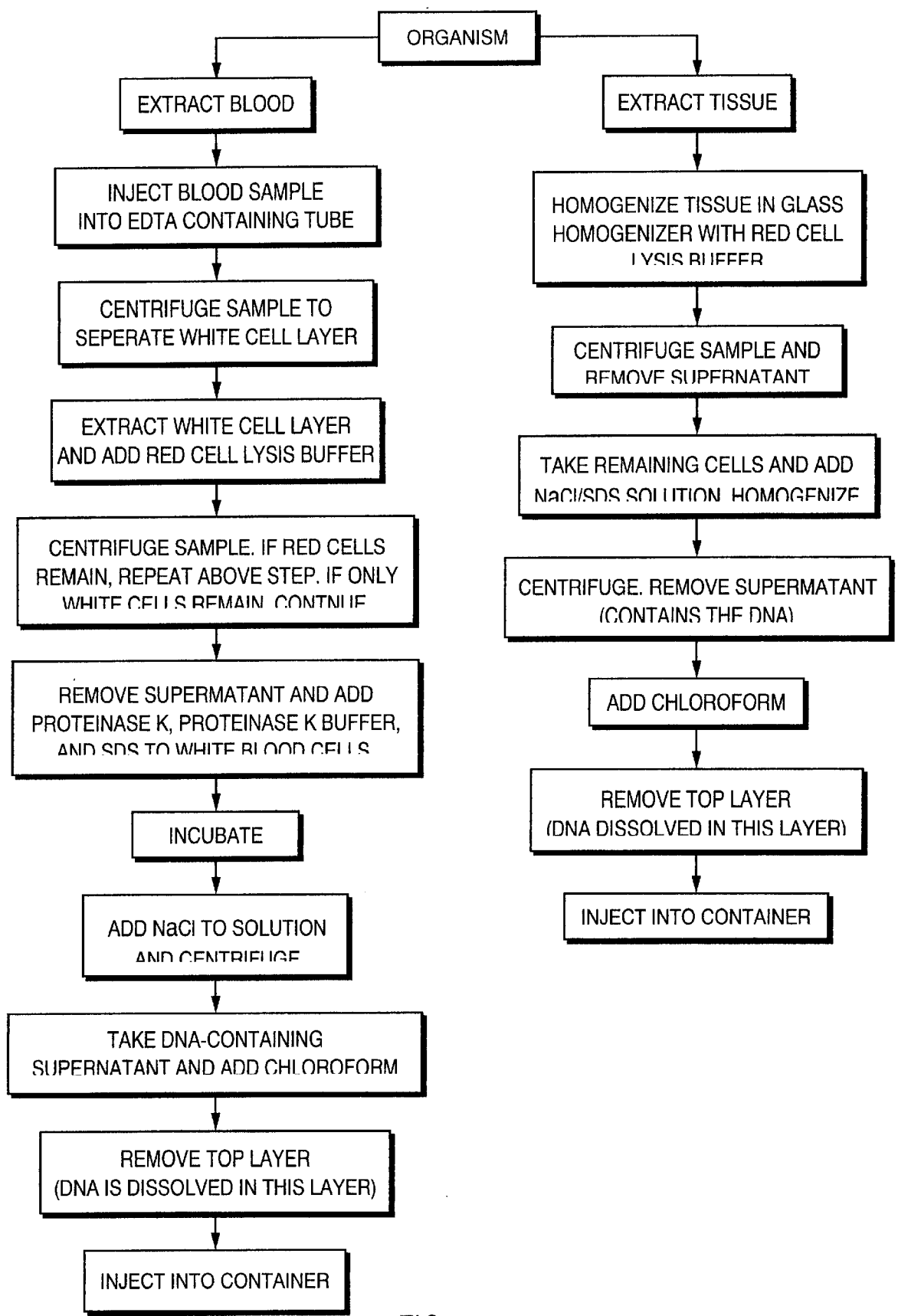
FIG. 3 is a flow diagram covering the DNA isolation and preservation process steps according to one embodiment of the invention.
Figure 4:
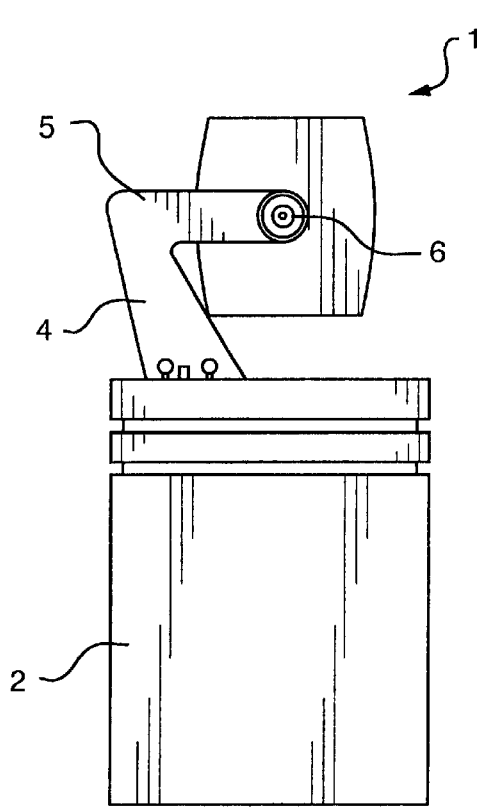
FIG. 4 is a side elevational view of a DNA display device according to one embodiment of the invention.
Figure 6:
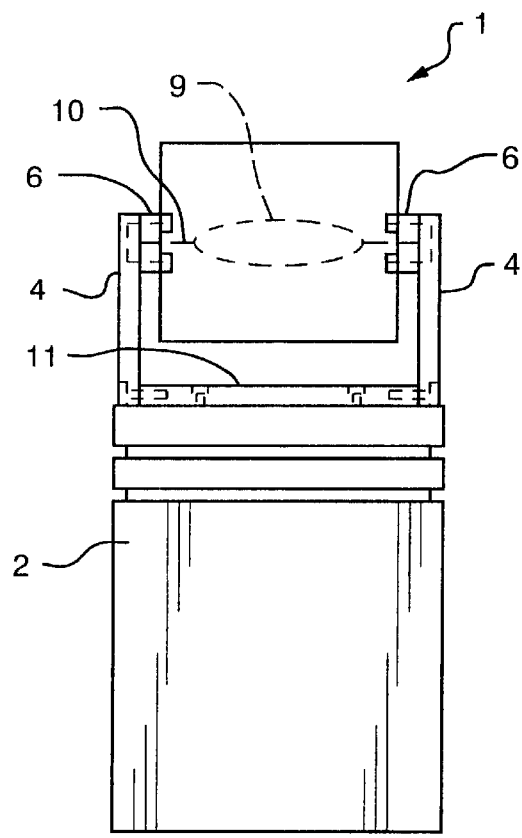
FIG. 6 is a front elevational view of a DNA display device according to one embodiment of the invention.
Figure 7:
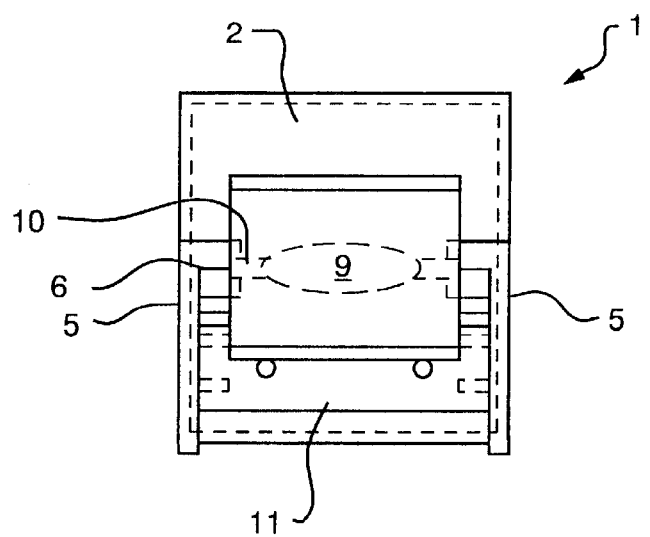
FIG. 7 is a top view of a DNA display device according to one embodiment of the invention.
Figure 5:
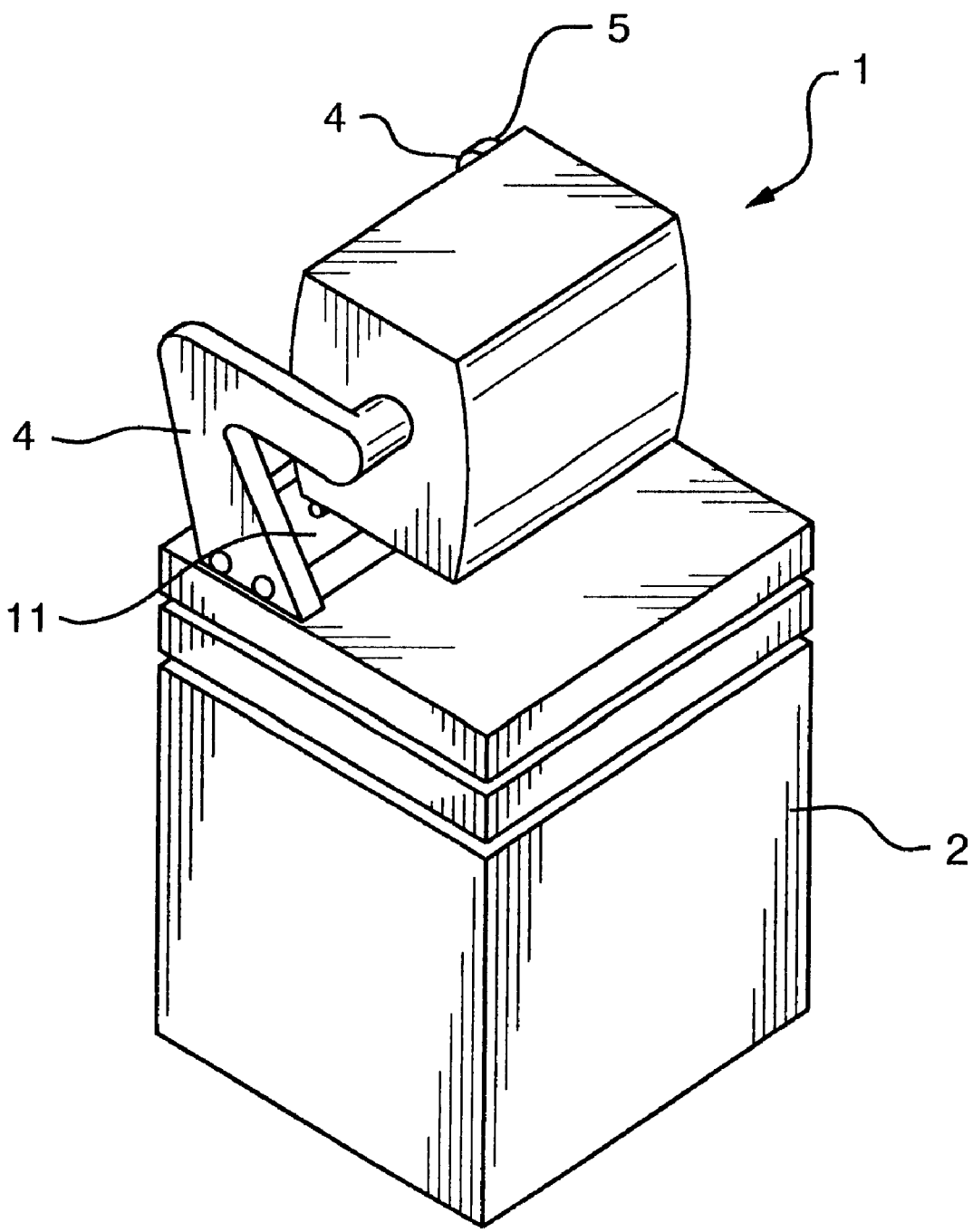
FIG. 5 is a top perspective view of a DNA display device according to one embodiment of the invention.

As shown in FIG. 3, the process of isolating and preserving DNA begins by obtaining tissue samples from an individual. The samples taken can be from any organism, plant or animal that has DNA bearing cells. In one embodiment, about 2 to 5 milliliters of blood is drawn and expelled into a test tube that is placed in a centrifuge. Preferably about 0.1 ml of about 0.5M EDTA (ethylenediaminetetraacetic acid) is added to about 5 ml of the blood sample to prevent coagulation. For expediency, the blood/EDTA mixture is centrifuged at approximately 2000 g for about 10 minutes to effectuate separation of the various blood components, e.g., red and white blood cells and plasma, based on density. It will be appreciated by those having skill in the art that the centrifuge speed and time can be altered without damaging the cells. Alternatively, the test tube can be allowed to sit for about 12 to 24 hours to allow the blood components to settle into layers.

A middle centrifuge layer containing white blood cells is isolated and placed in a second test tube. To eliminate red blood cells that may be inadvertently collected with the white blood cells, red cell lysis buffer (RCLB) (0.32M sucrose, 1% Triton, 5 mM $MgCl_2$ and 10 mM tris-HCl) is added to lyse any red blood cells. The second test tube is preferably centrifuged to separate any lysed red blood cells from the white blood cells. With this separation step, the white blood cells form a layer on the bottom of the test tube. The supernatant is discarded. Once the white cell layer has been isolated, a visual inspection is made to determine the completeness of the white blood cell separation. If necessary, additional RCLB/centrifuge/supernatant discarding cycles can be employed to complete the isolation step and ensure a maximum yield and purity of white blood cells. The steps can be repeated as many times as is necessary to remove most, if not all, of the red blood cell material. Separation of the white cells from the other cellular components is not temperature dependent and can be performed within a temperature range that is preferably above freezing and below about 65° C.

To lyse the white blood cells, proteinase K (Sigma Corporation, St. Louis, Mo.) along with proteinase K buffer and 20% SDS (sodium dodecyl sulfate, also known as Laurel sulfate) is admixed with the white blood cells. The mixture is heated to from about 45° C. to about 65° C. and preferably about 55° C. for from about 1 to about 2 hours. More preferably, the mixture is heated to 37° C. for from about 12 to about 24 hours. It is believed that heating the white blood cells at a lower temperature over a longer period of time has a less deleterious effect on the DNA and is thus the preferred approach. However, it should be understood that the temperature and the heating time can be varied so long as the white blood cells are lysed and the DNA is not denatured.

After heating, a 5 M sodium chloride (NaCl) solution is added to the mixture to salt out the protein-based cellular material. Preferably, the volume of NaCl added is about 20% of the total volume of the mixture. The addition of NaCl causes the cells' DNA material to be released into the solution. The cell membranes and other cell organelles settle to the bottom and form a semi-solid layer. The DNA material is not affected by the NaCl and remains dissolved in the supernatant.

To ensure only DNA is left in the supernatant, chloroform in an amount preferably equal to the volume of the DNA-laden solution is added which dissolves all the cellular components except DNA. This results in the DNA being "cleaned" of all other cellular components. To add body to the DNA strands, sodium acetate in an amount preferably equal to about 5% of the total solution volume is added to the solution. The DNA laden supernatent (a primarily water based solution) is then added to ethanol until an about 80% concentration of ethanol is achieved. This causes the DNA to precipitate out of solution. Because DNA is insoluble in ethanol, the DNA strands take on the appearance of threads loosely organized into a spherical shape. The individual strands or groups of strands are visible and appear to float in the solution.

Ethanol acts as a preservative to prevent DNA degradation. Ethanol is the preferred choice for an alcohol preservative because it is completely miscible in water. Ethylene glycol, methanol and isopropyl alcohol are other suitable choices for the alcohol component due to their miscibility with water.

Preferably, from about 70% to about 90% and more preferably about 80% ethanol and from about 10% to about 30% and more preferably about 20% distilled water is used in the solution to achieve the desired DNA precipitation. The key element of the system is the relative concentrations of the alcohol to the water components of the solution. The right range of concentrations provide DNA strands that form a loose association that has an aesthetically pleasing appearance, i.e., a spherical ball of loosely assembled threads that appear to float in solution and have a whitish hue. Too high a concentration of alcohol will cause the DNA to precipitate out into a tight ball whereas two low a concentration of alcohol will not cause the DNA to precipitate out.

In an alternate embodiment, a tissue sample is taken from the organism and mixed with the RCLB in a glass homogenizer to homogenize the tissue. The sample is centrifuged. The supernatant is discarded. Proteinase K, Proteinase K buffer, SDS and NaCl in the amounts and concentrations specified for the blood embodiment are admixed with the remaining cells. The mixture is homogenized and centrifuged using the aforementioned spin rates and time. The supernatant that contains the DNA is placed in a second test tube. Chloroform in the amounts specified for the blood embodiment is added to the supernatant. Addition of the chloroform causes the supernatant to separate into layers. The top layer in which the DNA is dissolved is removed and added to the ethanol in the amounts and concentrations specified for the blood embodiment.

Figure 17:
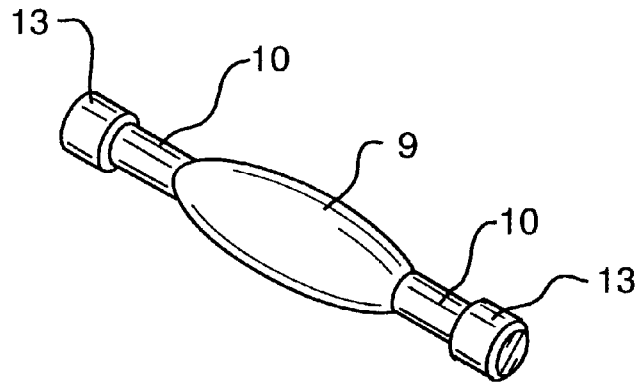
FIG. 17 is a side elevational view of a capsule according to one embodiment of the invention.
Figure 18:
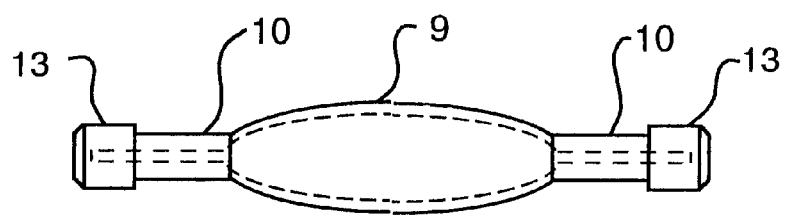
FIG. 18 is a side elevational view of a capsule according to one embodiment of the invention.
Figure 19:
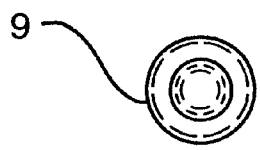
FIG. 19 is a top perspective view of capsule according to one embodiment of the invention.

Having processed the DNA to the point of suspension in the ethanol/$H_2O$ solution, the solution is delivered into a storage vial such as those shown in FIGS. 17–19, 21 and 22. Referring to FIGS. 17–19, a hollow capsule 9 used to contain the ethanol/$H_2O$ is shown. Capsule 9 is provided with opposed hollow extension arms 10 that have lumen in communication with a solution chamber formed in capsule 9. End caps 13 are provided on open ends of extension arms 10 and enable capsule 9 to be filled. End caps 13 can be secured to extension arms 10 with adhesive or via friction fit.

To fill capsule 9, a first end cap 13 is secured to first extension arm 10. The ethanol/H$_2$O solution is then poured into the open end of a second extension arm 10. Following completion of the solution-filling step, a second end cap 13 is secured to the second extension arm 10. Capsule 9 is then ready for display with or without the display device embodiments described below.

Figure 20:
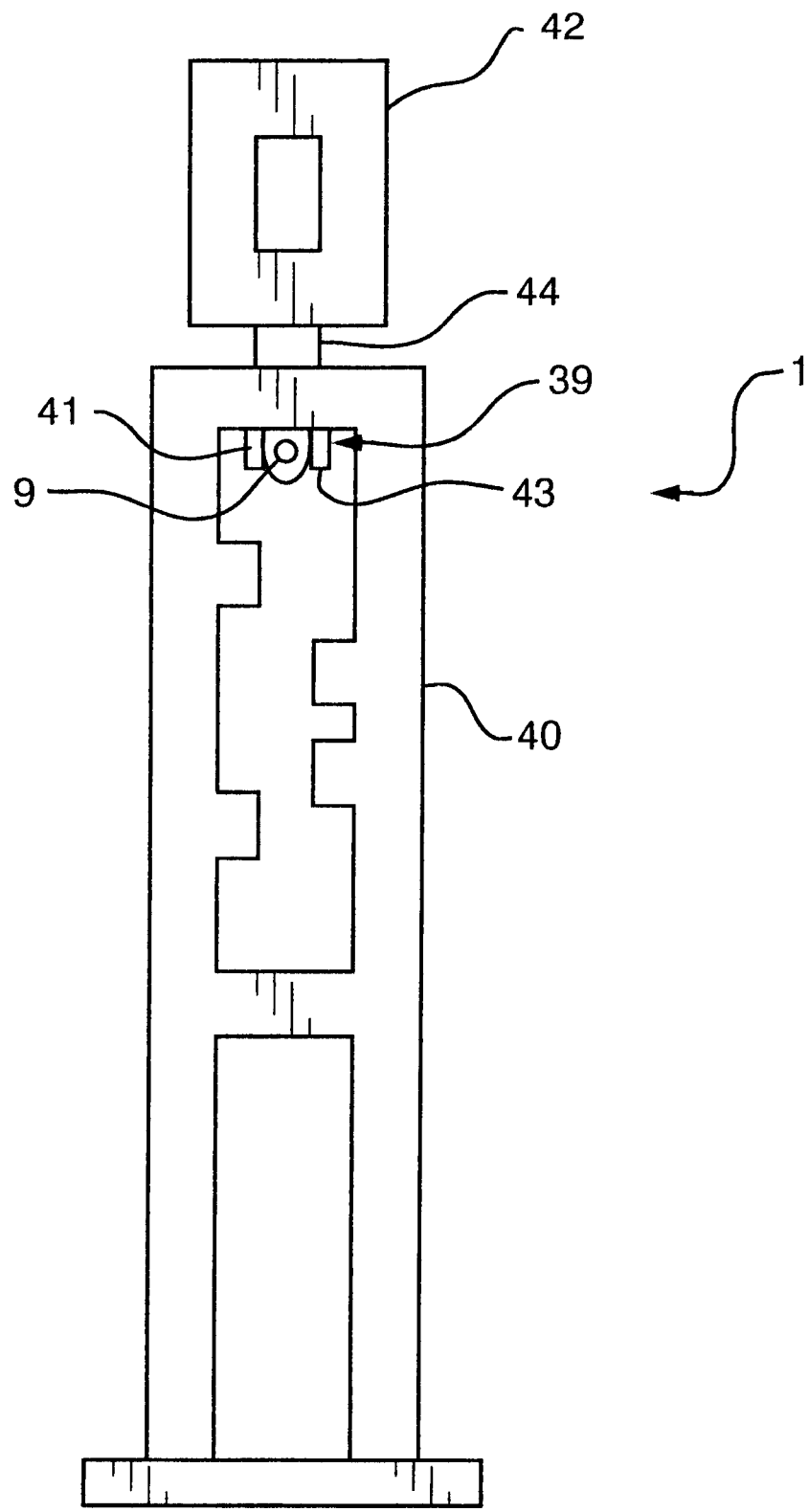
FIG. 20 is a front elevational view of a DNA display device according to a yet further embodiment of the invention.
Figure 21:
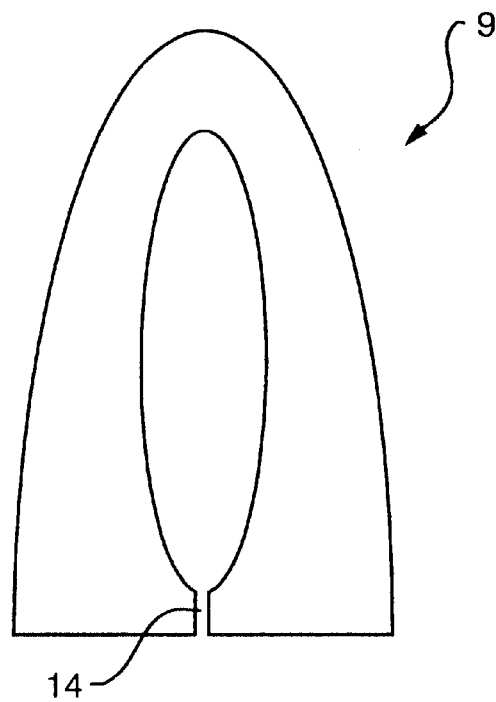
FIG. 21 is a front cross-sectional view of a capsule according to another embodiment of the invention.
Figure 22:
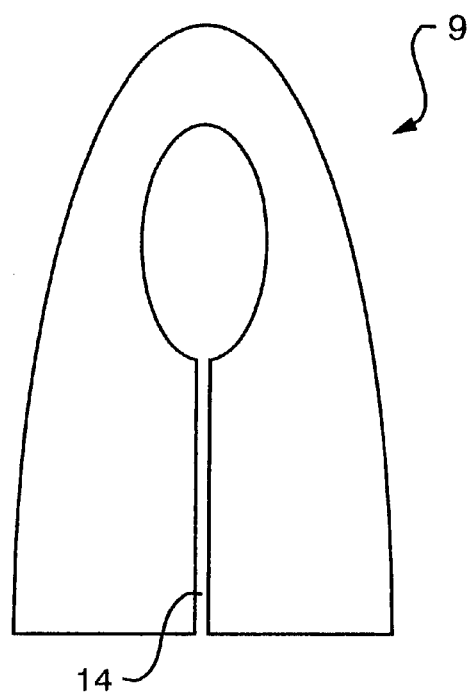
FIG. 22 is a cross-sectional view of a capsule according to yet another embodiment of the capsule according to one embodiment of the invention.

FIGS. 21 and 22 show alternative embodiments for capsule 9 that are particularly suitable for suspension in the display device shown in FIG. 20 described below. Capsule 9 as shown in FIG. 21 has a generally hyperbolic shape with an elongated solution chamber 12. A bore 14 is formed on a bottom end of capsule 9 to provide communication between chamber 12 and the exterior of capsule 9. The DNA solution is delivered into chamber 12 via bore 14. In this embodiment, capsule 9 is preferably made of blown glass.

FIG. 22 shows capsule 9 with a truncated solution chamber 12' and an elongated bore 14'. This embodiment provides a more compact enclosure for the DNA solution.

To fill either of the embodiments shown in FIGS. 21 and 22, the DNA solution is directed into bore 14 or 14'. The DNA solution is added until preferably a small bolus of air remains in solution chamber 12. Bore 14 or 14' is then sealed with an adhesive, such as an epoxy adhesive, wax plug or other suitable sealing means known to those having skill in the art. The seal should be watertight and not reactive with any of the DNA solution components or the material used to make the capsule such as acrylic.

Alternatively, ethanol can be pre-loaded into storage vial or capsule 9 to which the DNA containing solution is added. Once the DNA containing solution is sealed in capsule 9, the capsule is placed in a display device such as those shown in FIGS. 1, 2, 4–16 and 20.

Referring now to FIGS. 1 and 4–7, a capsule display device is shown generally as 1. The device has a base 2 upon which brackets 3 are attached. Brackets 3 have leg portions 4 that extend upwardly from base 2. Extending substantially horizontally from leg portions 4 are arms 5. Arms 5 have distal ends 6 from which extend opposing capsule receiving bores 7. Receiving bores 7 are spaced and adapted to each receive an end cap 13/extension arm 10 assembly such that extension arms 10 can rotate freely within receiving bores 7. A spacer 11 is provided on a top surface of base 2. Lateral portions of leg portions 4 are attached to opposing ends of spacer 11. Spacer 11 is sized to secure capsule 9 between distal ends 6 of arms 5. As shown in FIGS. 4–7, capsule 9 can be encased in a preferably transparent block of synthetic material such as acrylic.

Figure 1:
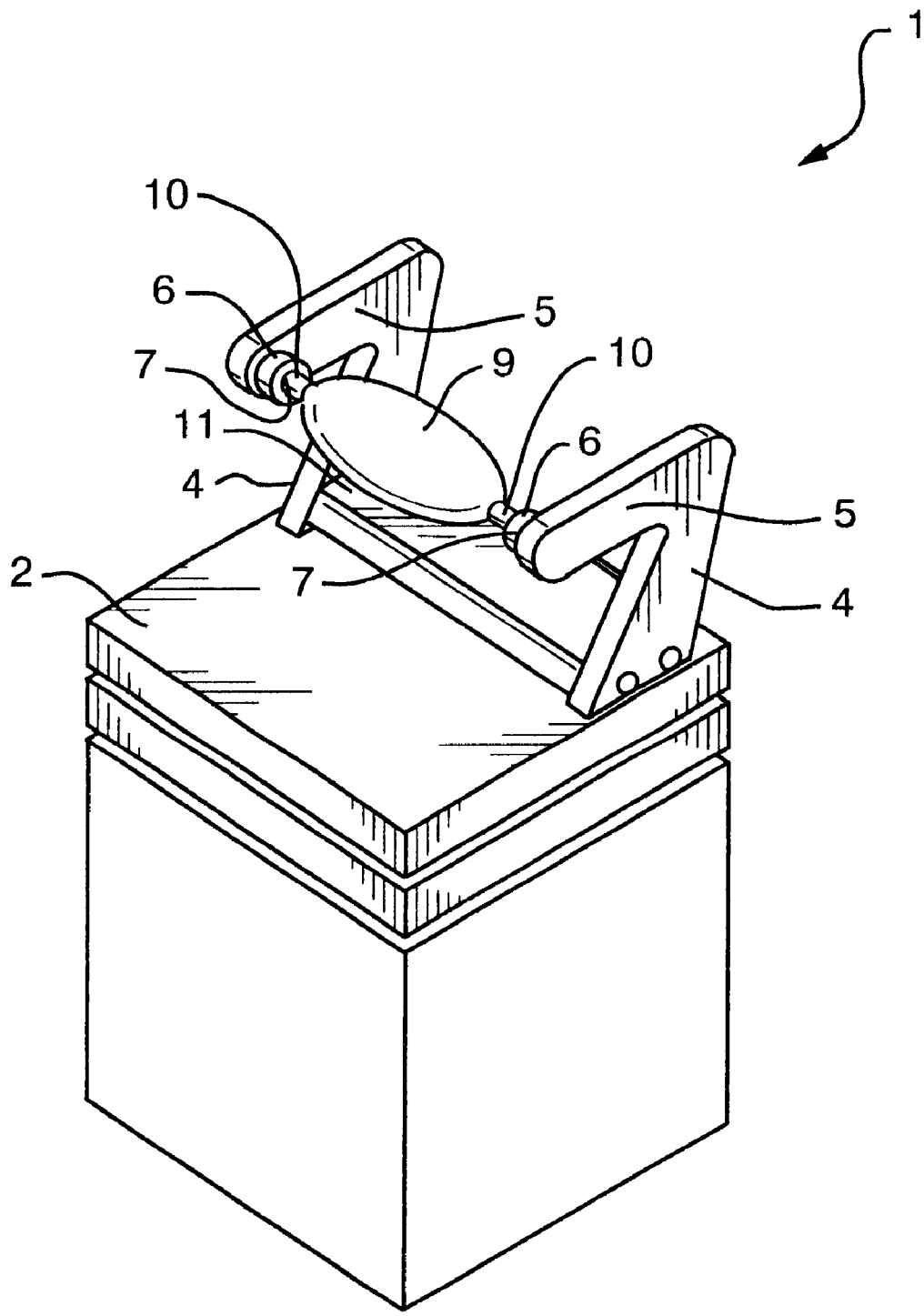
FIG. 1 is a perspective view of a DNA display capsule and stand according to one embodiment of the invention.
Figure 2:
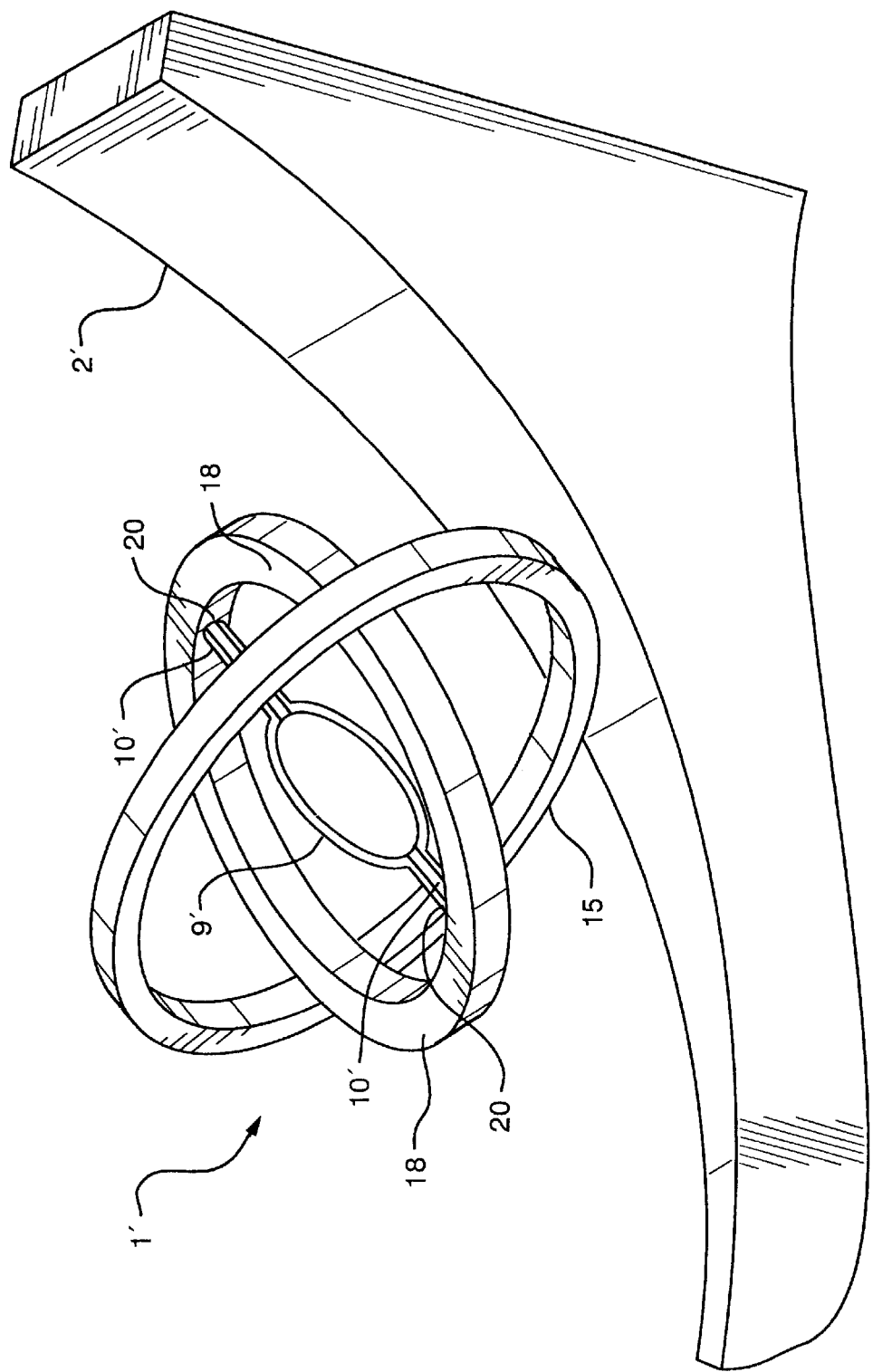
FIG. 2 is a perspective view of a DNA display capsule and stand according to another embodiment of the invention.
Figure 9:
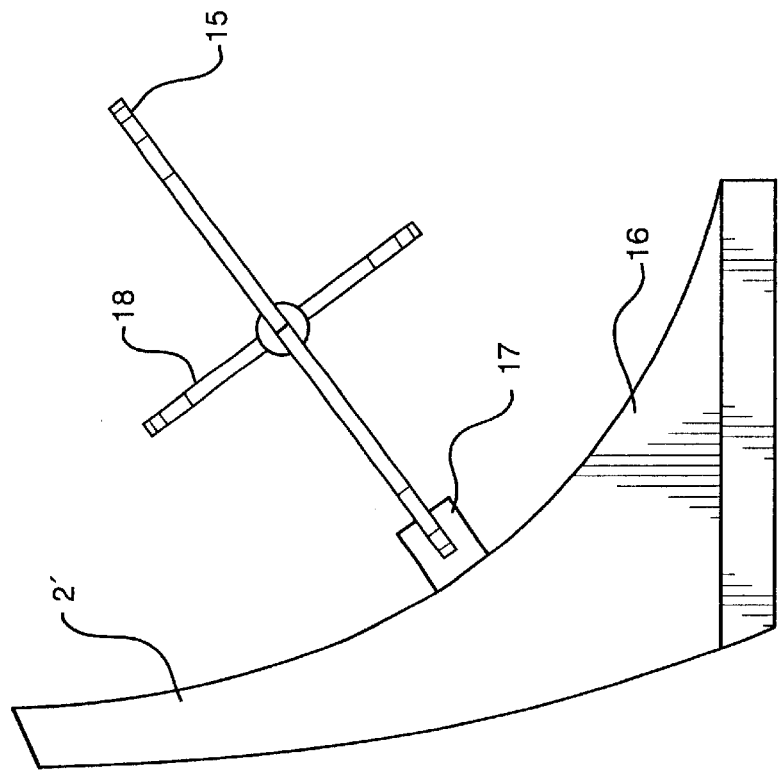
FIG. 9 is a side elevational view of a DNA display device according to another embodiment of the invention.
Figure 8:
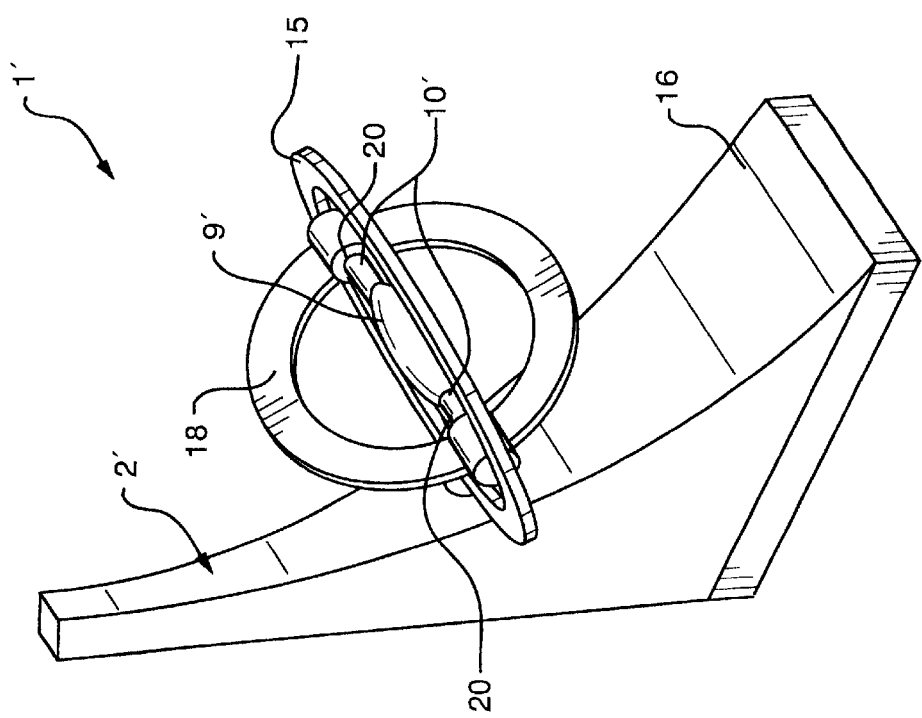
FIG. 8 is a top perspective view of a DNA display device according to another embodiment of the invention.
Figure 10:
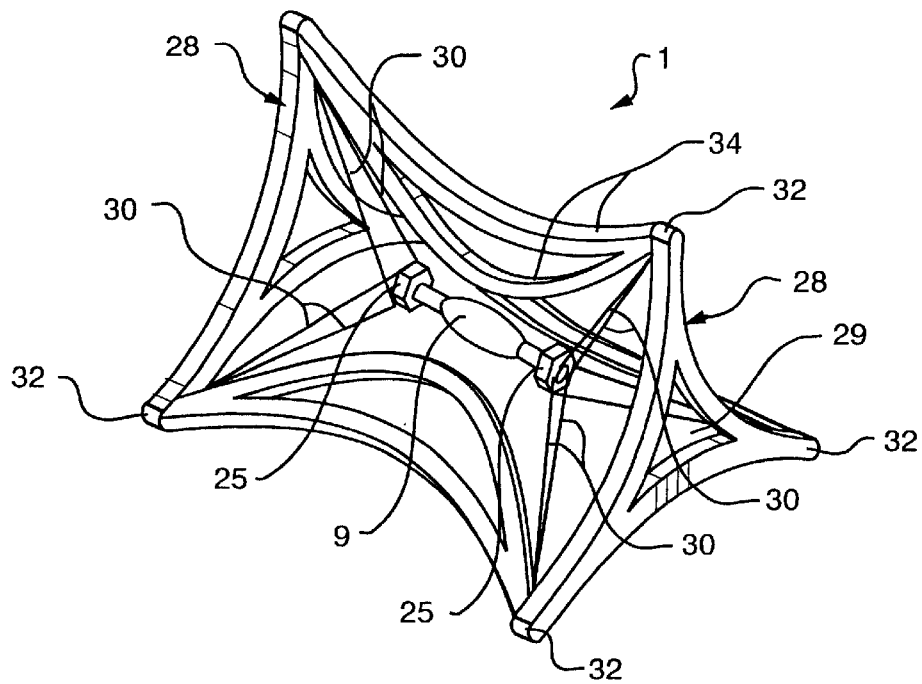
FIG. 10 is a top perspective view of a DNA display device according to a further embodiment of the invention.
Figure 11:
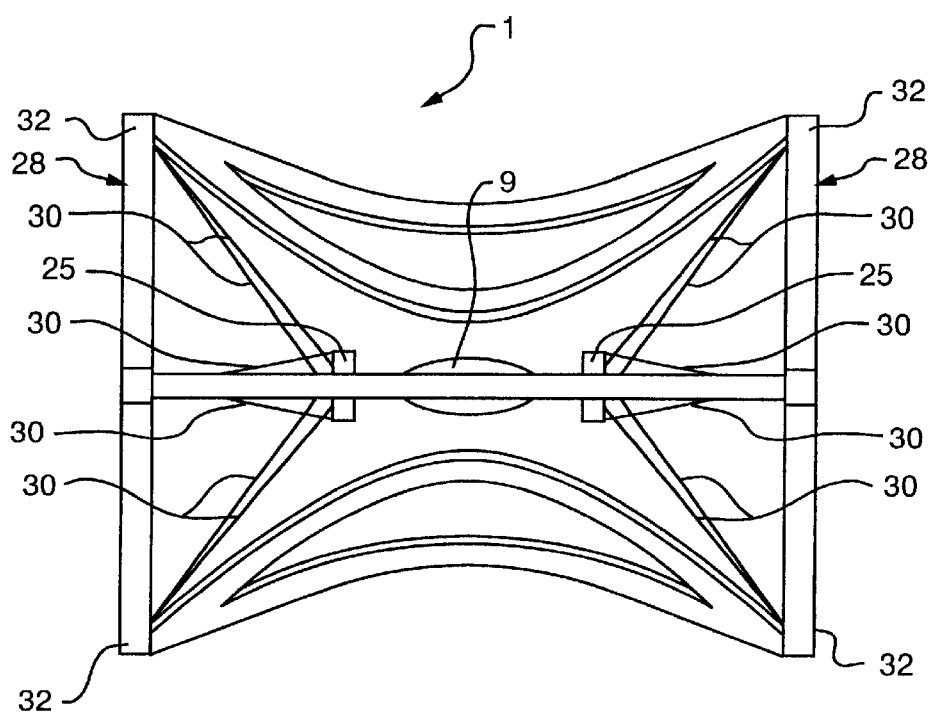
FIG. 11 is a top view of a DNA display device according to a further embodiment of the invention.
Figure 12:
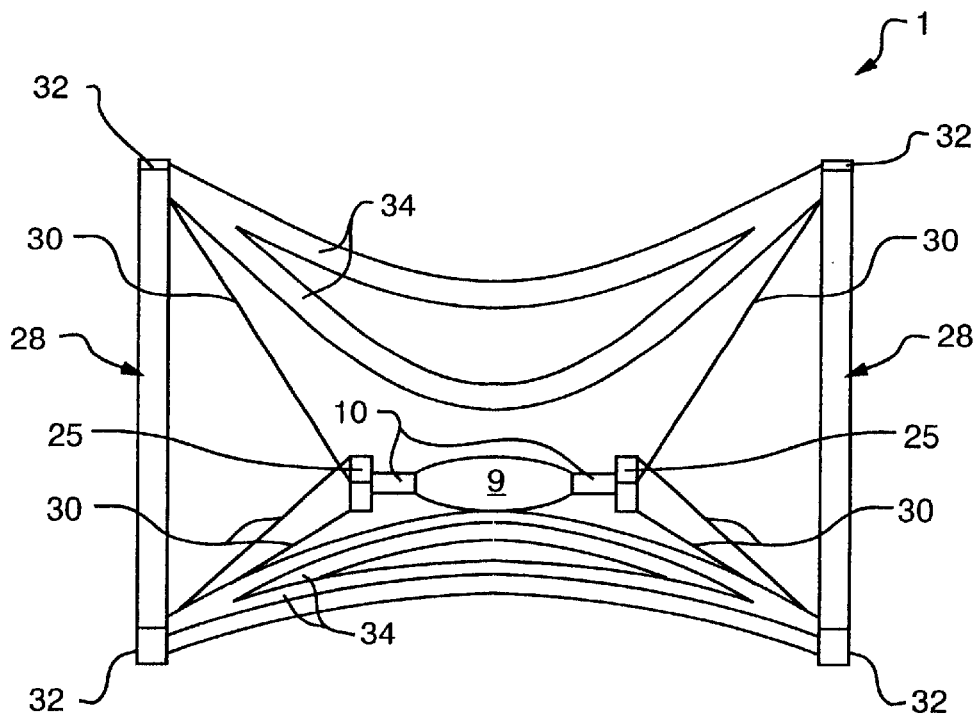
FIG. 12 is a front elevational view of a DNA display device according to a further embodiment of the invention.
Figure 13:
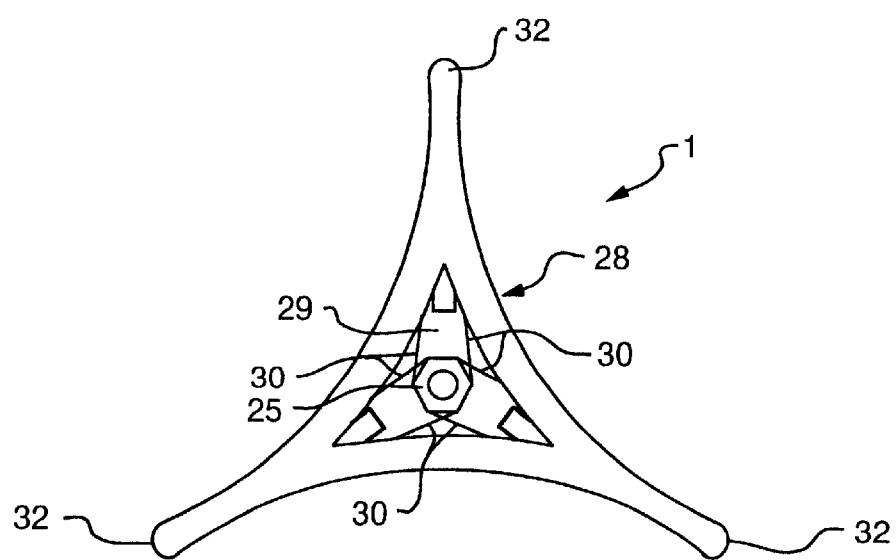
FIG. 13 is a side elevational view of a DNA display device according to a further embodiment of the invention.

FIGS. 2, 8 and 9 show another embodiment of the capsule display device 1'. Structures designated with prime numbers correspond to like structures in other embodiments designated with unprimed numbers. In this embodiment, base 2' is configured in the general shape of a half-pipe with a concave sidewall. A first circular ring 15 is attached at a point on its circumference to a mounting bracket 17 attached to the concave top surface 16 of base 2'. A second circular ring 18 having an outer diameter slightly less than the inner diameter of first circular ring 15 is attached at two points on its outer circumference to two points on the inner circumference of first circular ring 15. The contact points of first circular ring 15 and second circular ring 18 allow for the free rotation of second circular ring 18 within first circular ring 15. Diametrically opposed bores 20 are provided on the inner circumference of second circular ring 18 to receive capsule 9'. Opposed extension arms 10' are adapted to engage and freely rotate within opposed bores 20 such that capsule 9' can be rotated within second circular ring 18. In this embodiment, the rotation of second circular ring 18 within first circular ring 15 and capsule 9' within second circular ring 18 allows the display of the DNA to be varied to vary for example, the reflection of light from capsule 9'.

FIGS. 10–13 show a further embodiment of the display device adapted for suspended display. Capsule 9 is set within bearings 25 via extension arms 10 to allow free rotation of capsule 9. The capsule display device 1 is a frame comprised of end plates 28 that are generally triangular in shape with sides having concave profiles that combined form a triangular aperture 29. Suspension cables 30 attach bearings 25 to preferably each point 32 of end plates 28. End plates 28 are connected by three sets of dual concave struts 34. Struts 34 connect corresponding points 32. The structure of this embodiment of display device 1 has three symmetrical surfaces any of which can be used to support capsule 9 on a substrate. In this embodiment, display device 1 is preferably made of acrylic.

Figure 14:
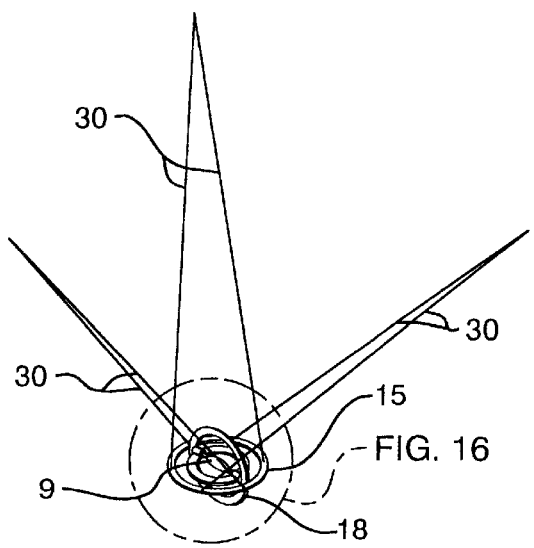
FIG. 14 is a top perspective view of a DNA display device according to still another embodiment of the invention.
Figure 15:
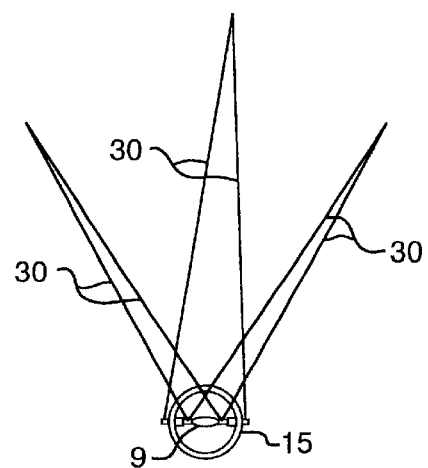
FIG. 15 is a side elevational view of a DNA display device according to still another embodiment of the invention.
Figure 16:
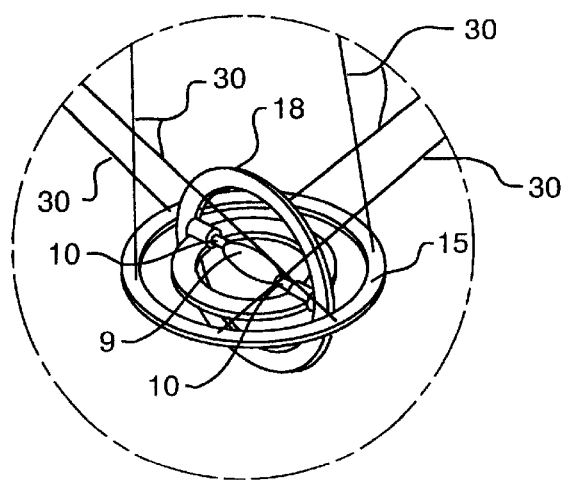
FIG. 16 is a magnified view of the DNA display device shown in FIG. 14.

A yet further embodiment of display device 1 is shown in FIGS. 14–16. In this embodiment, the rings of the second embodiment shown in FIG. 2 are combined with the suspension cables of the third embodiment shown in FIG. 12. Suspension cables 30 are attached to outer ring 15 and to a ceiling (not shown) or other substantially horizontal structure that is elevated to allow capsule 9 to be suspended.

A still further embodiment of display device 1 is shown in FIG. 20. In this embodiment, capsule 9 is nested in a housing 39 comprised of vertical rails 41 and a base 43 that has portions defining a capsule aperture (not shown) sized to receive and support capsule 9. Housing 39 is suspended from a first frame 40 configured to resemble and represent the torso and legs of a human being. A second frame 42 is attached to a top portion of first frame 40 via vertical segment 44. Second frame 42 and vertical segment 44 are configured to represent the head and neck of a human being, respectively. The frames can be made from wood or metal such as mahogany, brass and aluminum. This embodiment is designed to symbolize the human individual from whom DNA contained in capsule 9 has been extracted.

Capsule 9 shown in FIGS. 21 and 22 is adapted to be suspended with the convex portion of the capsule nested in a harness such as that shown in FIG. 20. The hyperbolic profile of these capsule embodiments allows the capsule to be secured in a harness with an aperture that has a diameter smaller than the greatest diameter of capsule 9. Capsule 9 is seated in the harness by orienting capsule 9 with the end having the smallest diameter facing downwardly.

Regardless of the device used to display the DNA, one of the keys to effectively display the DNA is to provide a storage vessel that can adjust for the expansion and contraction forces caused by changes in the ambient temperature and pressure. One method is to include a bolus of air in the sealed capsule. Another is the use of an expandable material such as plastics for capsule 9 and/or end caps 13 to adjust for expansion and contraction of the DNA containing solution.

The foregoing capsule and display device embodiments provide a method to preserve and display the uniqueness and identity of an individual organism by providing a vehicle for displaying DNA in a coalesced form that is visible to the naked eye. The method comprises extracting cellular material from a living being. The cellular material is broken down into its components and processed as described above so that the DNA portion of the cells can be isolated from the other cellular components. The DNA is suspended in a solution that causes its precipitation into a form that is visible. The solution is delivered into a capsule and display device as described above for final preservation and display.

It should be understood that the foregoing description of the invention is intended merely to be illustrative thereof and that other modifications, embodiments and equivalents may be apparent to those skilled in the art without departing from its principles. For example, the foregoing methods of isolating DNA can be used with any organism that has DNA-based genetic material. The methods can also be used to isolate ribonucleic acid (RNA) based genetic material although RNA is not as large or as stable as DNA. Moreover, RNA does not have an appearance as aesthetically pleasing as DNA.

Having thus described my invention, what I claim as new and desire to secure by Letters Patent is:

1. A DNA display device for preserving the uniqueness and identity of an organism comprising:
   a substantially transparent capsule having a cavity formed therein;
   a solution provided within the cavity; and,
   DNA from the organism wherein the DNA is precipitated and suspended in the solution and visible to an unaided eye.

2. The display device of claim 1 wherein the DNA is derived from an organism selected from the group consisting of human beings, animals, plants, bacteria or viruses.

3. The display device of claim 1 wherein the solution is a mixture of water and an alcohol selected from the group consisting of methanol, ethanol, ethylene glycol, isopropyl alcohol and mixtures thereof.

4. The display device of claim 3 wherein the solution is from about 70% to about 90% of the total volume ethanol and from about 10% to about 30% of the total volume water.

5. The display device of claim 3 wherein the solution comprises 80% of the total volume ethanol and 20% of the total volume water.

6. The display device of claim 1 wherein the solution is a mixture of water and an alcohol miscible in water.

7. The display device of claim 1 further comprising a capsule display device.

8. The display device of claim 7 wherein the capsule display device comprises:
   a base; and,
   two brackets attached to a top surface of the base and adapted to hold the capsule.

9. The display device of claim 8 wherein each of the two brackets comprises an elongate leg extending upwardly from the top surface of the base and a bracket arm attached at a first end to a top of the elongate leg and having a capsule receiving bore formed in a second end adapted to receive the capsule.

10. The display device of claim 9 wherein the capsule has capsule extensions adapted to be received in rotational engagement within the capsule receiving bores.

11. The display device of claim 7 wherein the capsule display device comprises:
   a base having a concave sidewall;
   a first ring attached at a point on its circumference to the concave sidewall;
   a second ring having an outer diameter less than an inner diameter of the first ring and attached to two points on an inner wall of the first ring such that the second ring freely rotates about the two points of attachment.

12. The display device of claim 11 wherein the second ring has portions defining at least one capsule receiving bore.

13. The display device of claim 12 wherein the second ring has portions defining two diametrically opposed capsule receiving bores for receiving extension arms of the capsule such that the capsule can be freely rotated within the receiving bores.

14. The display device of claim 7 wherein the capsule display device comprises:
   a frame having end plates each forming apertures and struts connecting the end plates;
   at least one bearing for receiving an extension arm of the capsule such that the capsule freely rotates within the bearing; and,
   at least one suspension cable attaching the at least one bearing to the frame.

15. The display device of claim 7 wherein the capsule display device comprises:
   a first ring;
   a second ring having an outer diameter less than the inner diameter of the first ring wherein the second ring is connected to the first ring at two points such that the second ring freely rotates about the two points; and,
   at least one suspension cable connected to the first ring for suspending the capsule display device from a substrate.

16. The display device of claim 15 wherein the second ring has portions defining two diametrically opposed capsule receiving bores for receiving extension arms of the capsule such that the capsule can be freely rotated within the receiving bores.

17. The display device of claim 7 wherein the capsule display device comprises a frame having portions resembling a human torso, portions resembling a human head and neck, portions resembling human legs and portions adapted to receive the capsule.

18. A method of preserving and displaying genetic material comprising:
   extracting genetic material from an organism;
   providing a solution;
   precipitating and suspending the genetic material in the solution to render it visible to the unaided eye; and
   displaying the genetic material in a substantially transparent capsule.

19. The method of claim 18 wherein the genetic material is selected from the group consisting of DNA and RNA.

20. The method of claim 18 wherein the genetic material precipitated and suspended in a solution of from about 70% to about 90% of a total solution volume of ethanol and from about 10% to about 30% of the total solution volume of water.

21. The method of claim 20 wherein the solution comprises 80% of the total volume ethanol and 20% of the total volume water.

22. The method of claim 19 wherein the genetic material is precipitated and suspended in a solution that is a mixture of water and an alcohol miscible in water.

23. A method of preserving the uniqueness and identity of an individual comprising the steps of:
   extracting a sample of blood from an organism;
   injecting the sample into a container containing ethylenediaminetetraacetic acid;
   centrifuging the sample to separate the blood into blood component layers including at least a white cell layer;
   extracting and placing the white cell layer in a second container;
   adding red cell lysis buffer to the white cell layer;

centrifuging the second container;

removing a supernatant from the second container;

adding proteinase K, proteinase K buffer and SDS to the second container;

incubating a solution contained in the second container;

adding NaCl to the second container;

centrifuging the second container containing the NaCl;

removing a second supernatant from the second container;

adding Chloroform to the second supernatant to form a second supernatant/Chloroform mixture;

removing a top layer of the second supernatant/Chloroform mixture wherein the top layer contains DNA; and precipitating and suspending the DNA in a mixture of water and an alcohol miscible in water.

24. The method of claim 23 comprising the further step of injecting the top layer the second supernatant/Chloroform mixture into a capsule.

25. A method of preserving the identity and uniqueness of an individual comprising the steps of:

extracting a tissue sample from a living being;

mixing the tissue sample with red cell lysis buffer to form a tissue sample/red cell lysis buffer mixture;

placing the tissue sample/red cell lysis buffer mixture in a glass homogenizer;

homogenizing the tissue sample/red cell lysis buffer mixture;

centrifuging the tissue sample/red cell lysis buffer mixture in a homogenizer;

removing a first supernatant from the homogenizer;

adding NaCl and SDS to the tissue sample/red cell lysis buffer mixture;

homogenizing the mixture;

centrifuging the mixture;

removing a second supernatant from the mixture;

adding Chloroform to the second supernatant to form a second supernatant/Chloroform mixture;

removing a top layer of the second supernatant/Chloroform mixture; and, precipitating DNA contained in the top layer by mixing it in a solution of water and an alcohol miscible in water.

26. The method of claim 25 wherein the solution comprises from about 70% to about 90% of a total solution volume ethanol and from about 10% to about 30% of the total solution volume water.

27. The method of claim 25 wherein the solution comprises 80% of the total volume ethanol and 20% of the total volume water.

28. The method of claim 25 wherein the amount of chloroform added to the second supernatant is from about 90% to about 110% of the amount of the second supernatant.

29. The method of claim 25 wherein the amount of Chloroform added to the second supernatant is equal to the amount of the second supernatant.

* * * * *